(12) United States Patent
Liang et al.

(10) Patent No.: US 10,059,698 B2
(45) Date of Patent: Aug. 28, 2018

(54) HESPERETIN AZA-CINNAMIC ACID DERIVATIVES WITH ANTI-TUMOR ACTIVITIES AND A METHOD OF PREPARING THE SAME

(71) Applicants: Chengyuan Liang, Xi'an (CN); Minyi Jia, Xi'an (CN); Yuecheng Lyu, Xi'an (CN); Xingke Ju, Xi'an (CN); Lei Tian, Xi'an (CN)

(72) Inventors: Chengyuan Liang, Xi'an (CN); Minyi Jia, Xi'an (CN); Yuecheng Lyu, Xi'an (CN); Xingke Ju, Xi'an (CN); Lei Tian, Xi'an (CN)

(73) Assignee: Shaanxi University of Science and Technology, Xi'an (CN)

( * ) Notice: Subject to any disclaimer, the term of this patent is extended or adjusted under 35 U.S.C. 154(b) by 0 days.

(21) Appl. No.: 15/719,924

(22) Filed: Sep. 29, 2017

(65) Prior Publication Data

US 2018/0186776 A1 Jul. 5, 2018

(30) Foreign Application Priority Data

Dec. 31, 2016 (CN) ............................ 2016 1 1266154
Aug. 2, 2017 (CN) ............................ 2017 1 0650015

(51) Int. Cl.
*C07D 405/12* (2006.01)

(52) U.S. Cl.
CPC .................................. *C07D 405/12* (2013.01)

(58) Field of Classification Search
CPC ....................................................... C07D 405/12
See application file for complete search history.

(56) References Cited

U.S. PATENT DOCUMENTS 7,244,751 B2 * 7/2007 Lu .......................... C07C 233/51
514/357

* cited by examiner

*Primary Examiner* — Erich A Leeser

(57) ABSTRACT

A hesperetin aza-cinnamic acid derivative has the following formula (I):

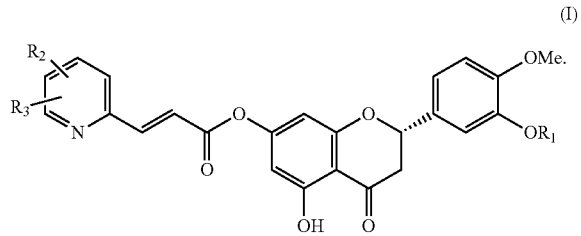

$R_1$ is H or alkyl, and $R_2$ and $R_2$ are independently H, alkyl, hydroxy, halogen, nitro, or alkoxy.

16 Claims, No Drawings

HESPERETIN AZA-CINNAMIC ACID DERIVATIVES WITH ANTI-TUMOR ACTIVITIES AND A METHOD OF PREPARING THE SAME

The present invention claims priority to Chinese Patent Application Nos. 201611266154.0, filed on Dec. 31, 2016, and 201710650015.6, filed on Aug. 2, 2017, both of which are incorporated by reference for all purposes as if fully set forth herein.

FIELD OF THE INVENTION

The present invention relates to the field of medicinal chemistry, and in particular, to hesperetin aza-cinnamic acid derivatives having antitumor activities and a method of preparing the same

BACKGROUND OF THE INVENTION

Cancer has become a serious threat to human health. Researchers are pursuing effective, safe, and low-toxicity small molecular anti-tumor drugs. With the development of medicinal chemistry, research on natural products with anti-tumor activities and the derivatives of these products became an important trend.

Cancer has become a serious threat to human health. It is essentially a genetic disease. Various environmental and genetic carcinogenic factors cause DNA damage in a synergistic or sequential manner, thereby activating proto-oncogenes and/or inactivating tumor suppressor genes, changing in apoptosis-regulating genes and/or DNA repair genes, and then causing abnormal expression level and the transformation of target cells. The transformed cells first have mostly clonal hyperplasia, and through a long multi-stage evolution process, one clone relatively unrestrictedly amplifies and selectively form subclones with different characteristics (heterogeneity), obtaining the ability to infiltrate and transfer (malignant transformation), and forming malignant tumors, mainly due to unreasonable diet, genetic factors, and environmental factors. The mechanism of action for antitumor drugs and the target of the drugs vary. Because tumor cells are prone to multidrug resistance, treatment often fails. Researchers are diligently and continuously searching for effective and safe anti-tumor drugs.

Hesperetin is a class of natural flavonoid compounds isolated from *citrus* genus. It has anti-inflammatory, anti-oxidation, anti-allergic reaction, cardiovascular and anti-tumor activities. Hesperetin is mainly derived from the hydrolysis of hesperidin, and its glycosides can hydrolyzed by human intestinal microbial. Hesperetin is the main active ingredient of the herbs Chenpi, Qingpi, *Citrus aurantium*. Studies have shown that hesperetin could reduce the toxicity of doxorubicin in rats. Hesperetin also has anti-tumor activities. Studies have shown that hesperetin can inhibit the proliferation of HepG2 cells in vitro, and there is a time-dependent and dose-effect relationship. The mechanism of hesperetin's inhibition of the growth of hepatocellular carcinoma cells may be that apoptosis is promoted by inducing G2 arrest and upregulation of Caspase-3 protein expression.

Hesperetin is widely available and has no side effects and unique biological activities. The synthesis and structural modification of hesperetin has become popular in the development of new drugs. Cinnamic acid, aza-cinnamic acid and their derivatives have antitumor activities. As one new drug research and development strategy, they can be used as lead compounds for further research to obtain candidate compounds with better efficacy. One example is histone deacetylase inhibitor (HDI) inhibitor, Chidamide (approved in 2014), which was inspired by the introduction of aza-cinnamic acid and its derivatives in the compound design.

There remains a need for effective and safe small molecular anti-tumor drugs. There is also no report of hesperetin aza-cinnamic acid derivatives.

SUMMARY OF THE INVENTION

In one embodiment, the present invention provides a hesperetin aza-cinnamic acid derivative having the following formula (I):

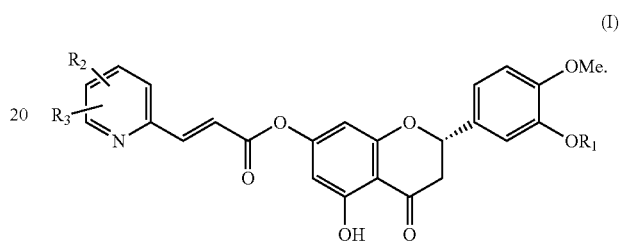

$R_1$ is H or alkyl, and $R_2$ and $R_3$ are independently H, alkyl, hydroxy, halogen, nitro, or alkoxy.

In another embodiment, the hesperetin aza-cinnamic acid derivative has the following formula (II):

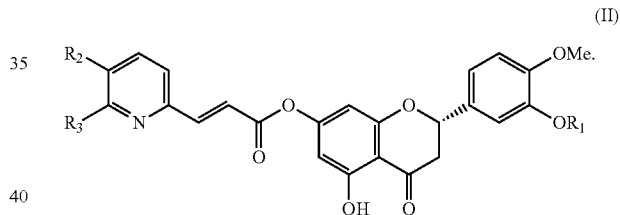

$R_1$ is H or alkyl, $R_2$ is H, alkyl, hydroxy, halogen, nitro, or alkoxy, and $R_3$ is H or alkoxy.

In another embodiment, the hesperetin aza-cinnamic acid derivative is:

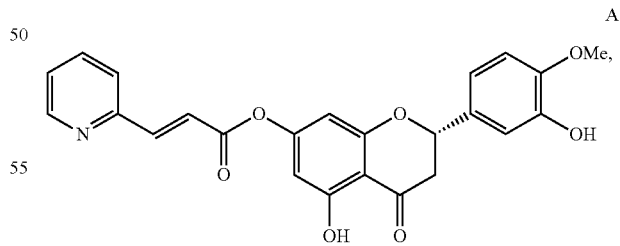

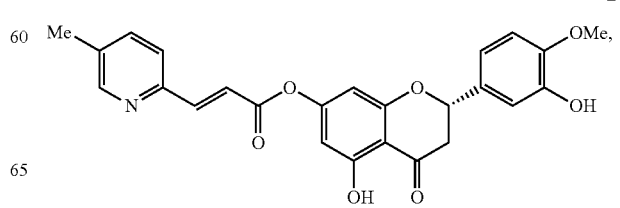

C
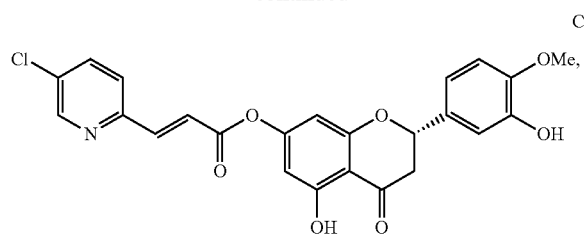
D
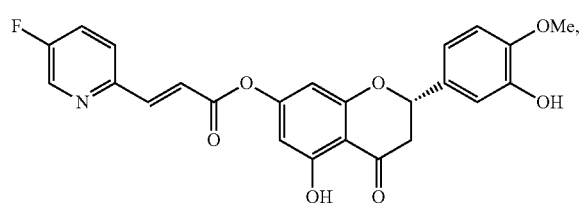
E
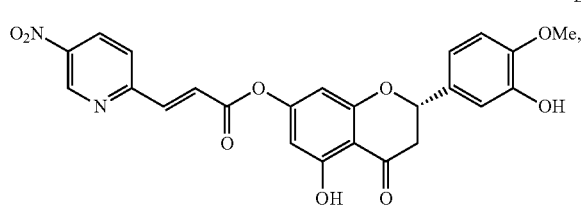
F
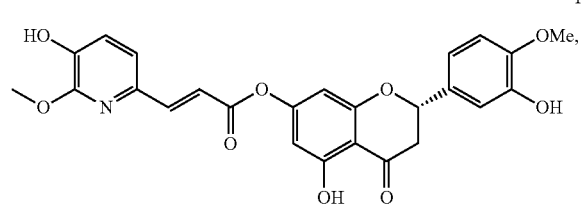
G
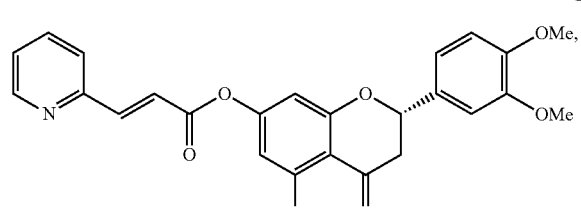
H
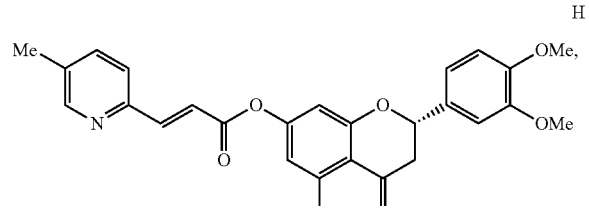
I
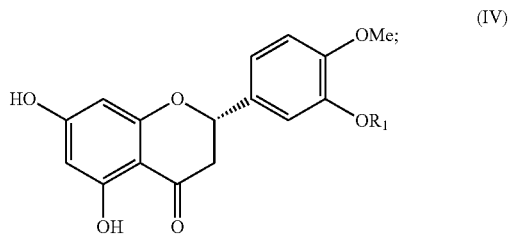
J
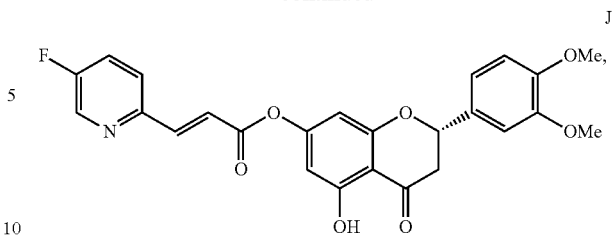
K
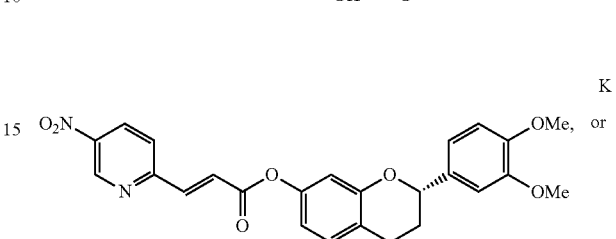
or
M
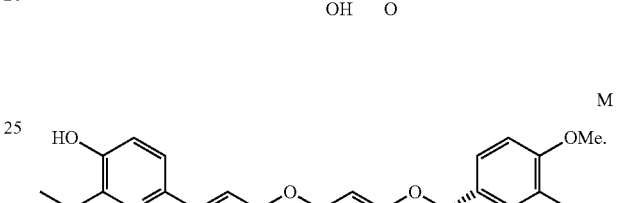
In one embodiment, the present invention provides a method of preparing hesperetin aza-cinnamic acid derivatives with antitumor activities comprising the following steps: (1) reacting a compound of formula (III):
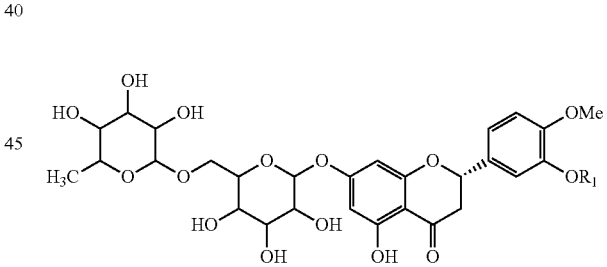
(III) with an acid to obtain a compound of formula (IV):
(IV)

and (2) reacting the compound of formula (IV) with a compound of formula (V):

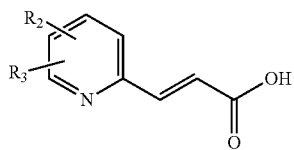

to obtain a hesperetin aza-cinnamic acid derivative of formula (I):

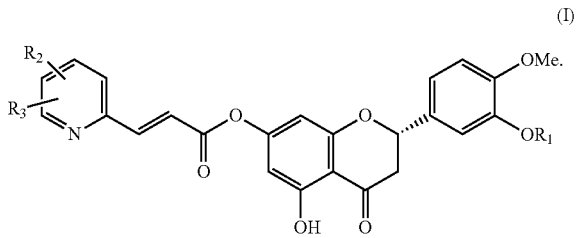

$R_1$ is H or alkyl, and $R_2$ and $R_3$ are independently H, alkyl, hydroxy, halogen, nitro, or alkoxy.

In another embodiment, in step (1), after the reaction of the compound of formula (III) with the acid is complete, the compound of formula (IV) is precipitated at a pH value of 5.

In another embodiment, in step (1), the acid is hydrochloric acid or sulfuric acid.

In another embodiment, in step (1), the reaction of the compound of formula (III) with the acid is conducted in an organic solvent selected from the group consisting of DMSO, acetonitrile, THF, DMF, and acetone.

In another embodiment, in step (1), the reaction of the compound of formula (III) with the acid is conducted at 90-110° C.

In another embodiment, in step (2), the reaction of the compound of formula (IV) with the compound of formula (V) is conducted in the presence of a base and DCC.

In another embodiment, in step (2), the base is sodium carbonate.

In another embodiment, in step (2), the reaction of the compound of formula (IV) with the compound of formula (V) is conducted in an organic solvent selected from the group consisting of DMSO, acetonitrile, THF, DMF, and acetone.

In another embodiment, in step (2), a molar ratio of the compound of formula (IV) and the compound of formula (V) is 1:1 to 1:1.5.

In another embodiment, the molar ratio of the compound of formula (IV) and the compound of formula (V) is 1:2.

In another embodiment, in step (2), the reaction of the compound of formula (IV) with the compound of formula (V) is conducted at 60-100° C.

In one embodiment, the present invention provides a method of using the hesperetin aza-cinnamic acid derivative in antitumor drug research, development, and application.

In one embodiment, the present invention provides a method of using the hesperetin aza-cinnamic acid derivative of claim 1 in treating human Lung cancer, liver cancer, glioma, gastric adenocarcinoma or breast cancer.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

As used herein, the term alkyl refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl. Alkoxy refers to an alkyl ether group wherein the alkyl moiety is as defined above.

The term halogen refers to fluorine, chlorine, bromine and iodine.

It is an object of the present invention to provide compounds with anti-tumor activities and a method of preparing the same. The method has the advantages of low-cost and abundant raw material, low production cost, high operational safety, mild conditions, high yields, suitable for industrial production. The hesperetin aza-cinnamic acid derivatives can be used in cancer research and to treat various cancers.

To achieve the above objects, the technical solution adopted by the present invention is described in details below.

A hesperetin aza-cinnamic acid derivative with anti-tumor activities has the following formula (I):

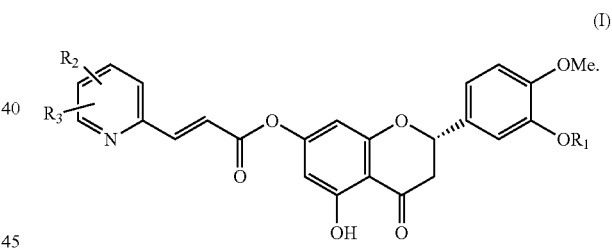

$R_1$ is H or alkyl, and $R_2$ and $R_3$ are independently H, alkyl, hydroxy, halogen, nitro, or alkoxy.

Preferably, the hesperetin aza-cinnamic acid derivative has the following formula (II):

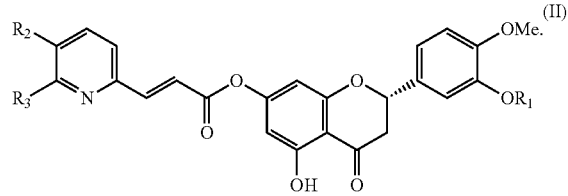

$R_1$ is H or alkyl, $R_2$ is H, alkyl, hydroxy, halogen, nitro, or alkoxy, and $R_3$ is H or alkoxy.

A method of preparing a hesperetin aza-cinnamic acid derivative of formula (I) using hesperidin and its derivatives (formula (III)), aza-cinnamic acid and its derivatives (formula (V)) as starting materials. The method includes 2 steps.

Step 1:

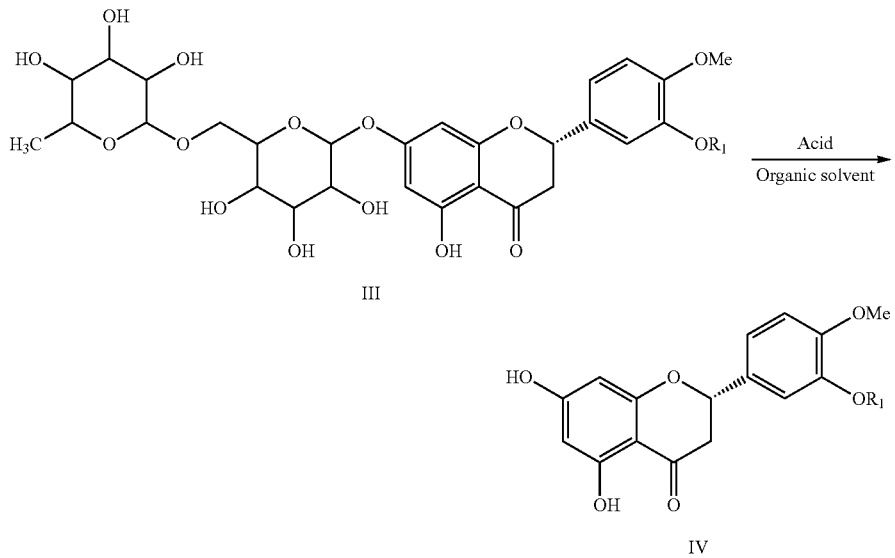

Hesperidin and its derivatives (formula (III)) was dissolved in an organic solvent and placed in a reaction flask. Acid was added, and the reaction mixture was reacted at 90-110° C. for 1-3 hours. The pH of reaction mixture was adjusted to about 4-6 to form a precipitate, and the reaction mixture was then filtered to give an intermediate (formula (IV), hesperetin and its derivatives). In formulas III and IV, $R_1$ is H or alkyl.

Step 2:

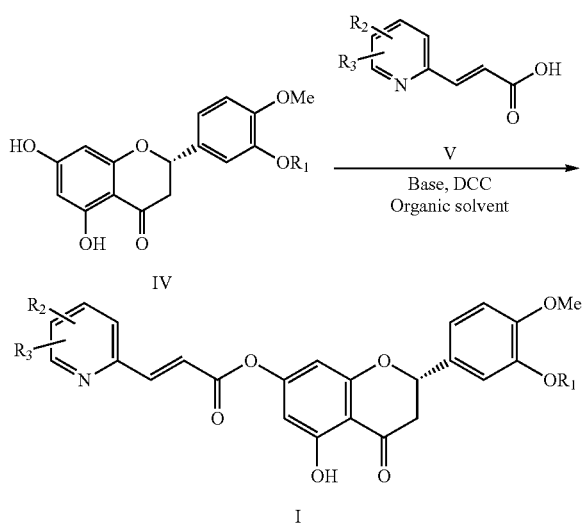

The intermediate (formula (IV)) and aza-cinnamic acid and its derivatives (formula (V)) were placed in a react flask in a molar ratio of 1:1 to 1:1.5. Organic solvent, base, and DCC were added and refluxed at 60-100° C. for 4-6 hours to obtain the desired product, the hesperetin aza-cinnamic acid derivative of formula (I). In formulas (I), (IV), and (V), $R_1$ is H or alkyl, $R_2$ is H, alkyl, hydroxy, halogen, nitro, or alkoxy, and $R_3$ is H or alkoxy.

Preferably, in step (1), the pH of reaction mixture was adjusted to about 5 to form a precipitate.

Preferably, in steps (1) and (2), the organic solvent is DMSO, acetonitrile, THF, DMF, or acetone; in step (1), the acid is hydrochloric acid or sulfuric acid; and in step (2), the base is potassium carbonate, potassium hydroxide, or sodium carbonate.

Preferably, in steps (1) and (2), the organic solvent is DMSO.

Preferably, in step (1), the acid is sulfuric acid.

Preferably, in step (2), a molar ratio of the intermediate (formula (IV)) and aza-cinnamic acid and its derivatives (formula (V)) is 1:1.2.

Preferably, in step (2), the reflex time is 5 hours.

Preferably, the base is sodium carbonate.

In the present application, DCC is N,N'-dicyclohexylcarbodiimide; DMSO is dimethyl sulfoxide; DMF is dimethylformamide; and THF is tetrahydrofuran.

Twin-drug refers to a new molecule that binds two identical or different lead compounds or drugs via a covalently bond, and this new molecule generates two drugs in vivo and produces synergistic effects, thus enhancing activity or increasing selectivity.

Advantages and benefits of the present invention: Hesperetin and aza-cinnamic acid are combined to form hesperetin aza-cinnamic acid derivatives according to the idea of twindrug. The novel chemical entity of hesperetin aza-cinnamic acid derivatives influence binding to receptor binding sites, improve bioavailability and biological activity, and reduce adverse drug reactions.

Based on this idea, a synthetic route using hesperidin as the key raw material is developed. The synthetic route of the hesperetin aza-cinnamic acid derivatives has the advantages of low-cost and abundant raw material, low production cost, high operational safety, mild conditions, high yields, suitable for industrial production.

In vitro antitumor activity tests show that some hesperetin aza-cinnamic acid derivatives have better anti-tumor activities than hesperetin. The hesperetin aza-cinnamic acid derivatives can be used in cancer research and to treat various cancers.

The present invention will now be described in further detail with reference to specific inventive examples below, but the present invention is not limited to the following examples.

Representative examples of the hesperetin aza-cinnamic acid derivatives of the present invention are as follows:

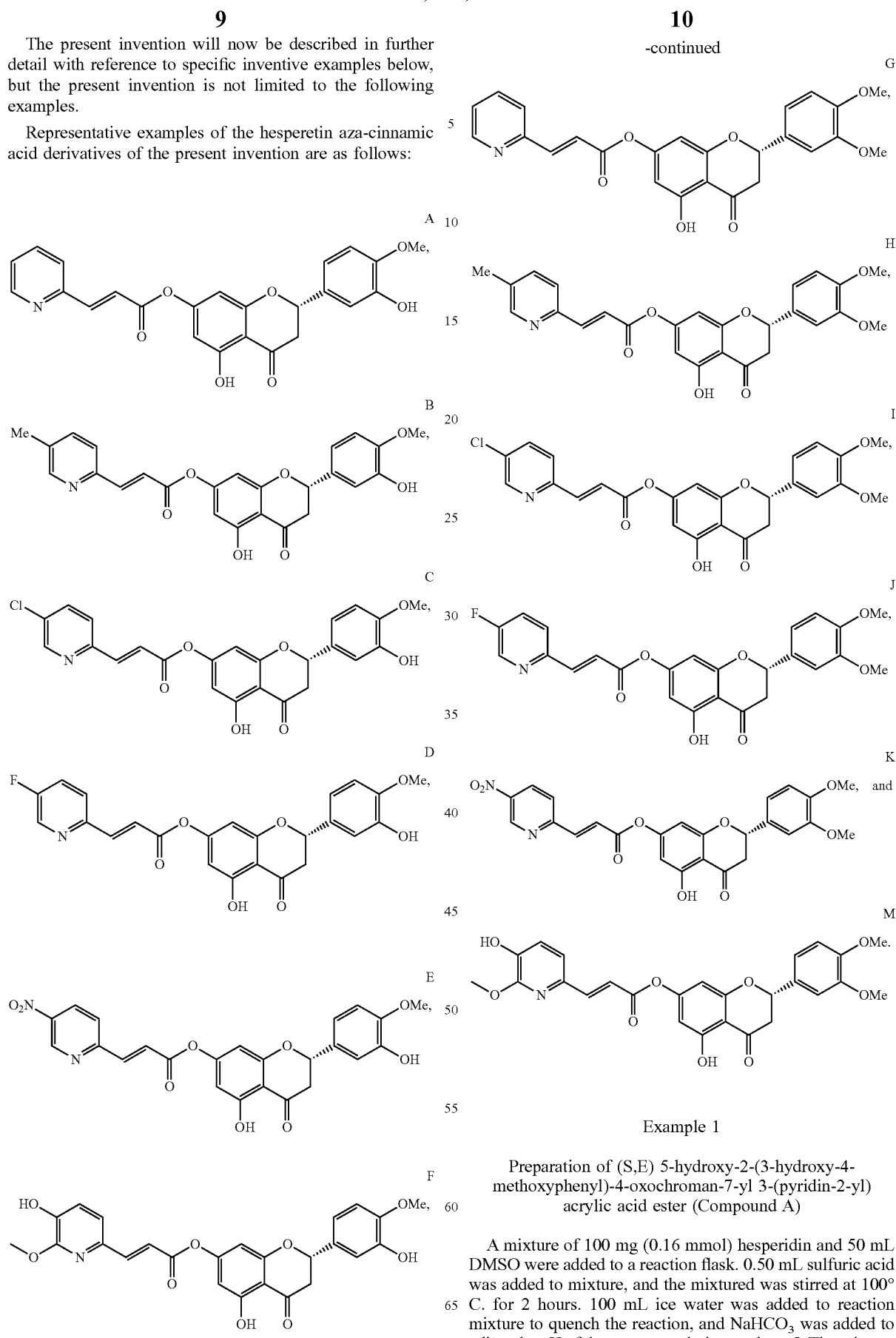

Example 1

Preparation of (S,E) 5-hydroxy-2-(3-hydroxy-4-methoxyphenyl)-4-oxochroman-7-yl 3-(pyridin-2-yl) acrylic acid ester (Compound A)

A mixture of 100 mg (0.16 mmol) hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 30 mg (0.2 mmol) (E)-3-(pyridin-2-yl) acrylic acid were dissolved in 40 mL DMF. 0.5 g DCC was added as a dehydrating agent. 0.45 g sodium carbonate was added to the reaction mixture, and reaction mixture was refluxed at 60-100° C. for 5 hours. The reaction mixture was cooled to room temperature. Water was added to the reaction mixture, and the mixture was then extracted with ethyl acetate. The ethyl acetate layer was concentrated, and purification by flash column chromatograph to give 35.3 mg (yield: 81.5%) desired product with the following structure.

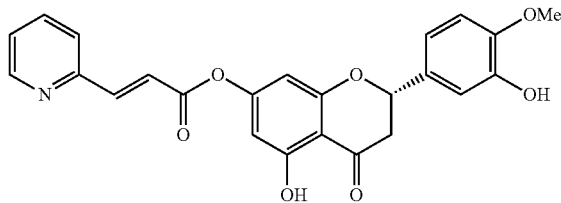 [SMILES: COc1ccc([C@@H]2CC(=O)c3c(O)cc(OC(=O)/C=C/c4ccccn4)cc3O2)cc1O]

$^1$H-NMR (300 MHz, DMSO-d6) δ (ppm): 8.45 (1H, d), 7.83 (1H, d, J=7.5 Hz), 7.43-7.29 (3H, m), 7.01 (1H, s), 6.92 (1H, d, J=7.5 Hz), 6.81-6.75 (2H, m), 6.54 (1H, s), 6.46 (1H, s), 5.52 (1H, t), 5.33 (2H, s), 3.85 (3H, s), 3.38-3.13 (2H, m); $^{13}$C-NMR (75 MHz, DMSO-d6) δ (ppm): 197.0, 164.1, 162.7, 157.8, 154.7, 148.9, 147.1, 142.0, 137.2, 131.0, 124.5, 122.4, 121.4, 120.0, 113.4, 107.0, 102.9, 83.0, 56.3, 43.1; MS (ESI) for (M+H)$^+$: 434.1.

Example 2

Preparation of (S,E) 5-hydroxy-2-(3-hydroxy-4-methoxyphenyl)-4-oxochroman-7-yl 3-(5-methyl-pyridin-2-yl) acrylate acid ester (Compound B)

A mixture of 100 mg (0.16 mmol) hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 32.6 mg (0.2 mmol) (E)-3-(5-methylpyridin-2-yl) acrylic acid were dissolved in 40 mL DMF. 0.5 g DCC was added as a dehydrating agent. 0.45 g sodium carbonate was added to the reaction mixture, and reaction mixture was refluxed at 60-100° C. for 6 hours. The reaction mixture was cooled to room temperature. Water was added to the reaction mixture, and the mixture was then extracted with ethyl acetate. The ethyl acetate layer was concentrated, and purification by flash column chromatograph to give 35.6 mg (yield: 79.6%) desired product with the following structure.

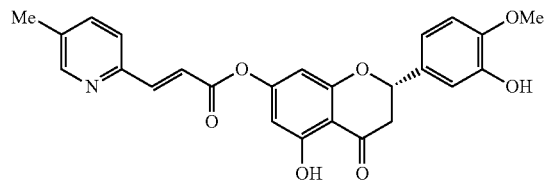 [SMILES: COc1ccc([C@@H]2CC(=O)c3c(O)cc(OC(=O)/C=C/c4ccc(C)cn4)cc3O2)cc1O]

$^1$H-NMR (300 MHz, DMSO-d6) δ (ppm): 8.35 (1H, s), 7.83 (1H, d, J=7.5 Hz), 7.45 (1H, d, J=7.6 Hz), 7.32 (1H, d, J=7.6 Hz), 7.01 (1H, s), 6.92 (1H, d, J=7.5 Hz), 6.81-6.75 (2H, m), 6.54 (1H, s), 6.46 (1H, s), 5.52 (1H, t), 5.33 (2H, s), 3.85 (3H, s), 3.38-3.13 (2H, m), 2.32 (3H, s); $^{13}$C-NMR (75 MHz, DMSO-d6) δ (ppm): 197.0, 164.1, 162.7, 157.8, 152.6, 149.3, 147.5, 142.0, 136.3, 132.6, 130.6, 121.4, 120.0, 113.4, 107.2, 103.3, 102.5, 83.0, 56.3, 43.1, 18.2; MS (ESI) for (M+H)$^+$: 448.1.

Example 3

Preparation of (S,E) 5-hydroxy-2-(3-hydroxy-4-methoxyphenyl)-4-oxochroman-7-yl 3-(5-chloro-pyridin-2-yl) acrylate acid ester (Compound C)

A mixture of 100 mg (0.16 mmol) hesperidin and 50 mL DMSO were added to a reaction flask. 1.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 36.7 mg (0.2 mmol) (E)-3-(5-chloropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 6 hours. The reaction mixture was cooled to room temperature. Water was added to the reaction mixture, and the mixture was then extracted with ethyl acetate. The ethyl acetate layer was concentrated, and purification by flash column chromatograph to give 16.62 mg (yield: 36.4%) desired product with the following structure.

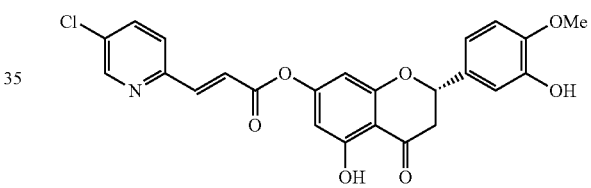

$^1$H-NMR (300 MHz, DMSO-d6) δ (ppm): 8.53 (1H, s), 7.83 (1H, d, J=7.5 Hz), 7.75 (1H, d, J=7.6 Hz), 7.60 (1H, d, J=7.6 Hz), 7.01 (1H, s), 6.92 (1H, d, J=7.5 Hz), 6.81-6.75 (2H, m), 6.54 (1H, s), 6.46 (1H, s), 5.52 (1H, t), 5.33 (2H, s), 3.85 (3H, s), 3.38-3.13 (2H, m); $^{13}$C-NMR (75 MHz, DMSO-d6) δ (ppm): 197.0, 164.1, 162.7, 157.8, 153.1, 151.5, 149.3, 147.5, 142.0, 135.8, 132.6, 130.6, 121.4, 120.0, 113.4, 107.2, 103.3, 102.5, 83.0, 56.3, 43.1; MS (ESI) for (M+H)$^+$: 468.1.

Example 4

Preparation of (S,E) 5-hydroxy-2-(3-hydroxy-4-methoxyphenyl)-4-oxochroman-7-yl 3-(5-fluoro-pyridin-2-yl) acrylate acid ester (Compound D)

A mixture of 100 mg (0.16 mmol) hesperidin and 50 mL DMSO were added to a reaction flask. 1.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 33.4 mg (0.2 mmol) (E)-3-(5-fluoropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 5 hours. The reaction mixture was cooled to room temperature. Water was added to the reaction mixture, and the mixture was then extracted with ethyl acetate. The ethyl acetate layer was concentrated, and purification by flash column chromatograph to give 26.20 mg (yield: 58.1%) desired product with the following structure.

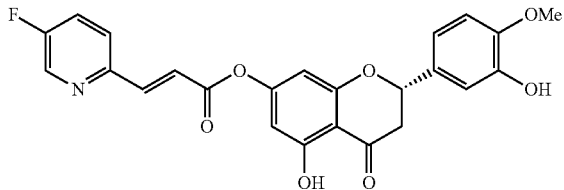 [SMILES: COc1ccc([C@@H]2CC(=O)c3c(O)cc(OC(=O)/C=C/c4ccc(F)cn4)cc3O2)cc1O]

¹H-NMR (300 MHz, DMSO-d6) δ (ppm): 8.36 (1H, d), 7.83 (1H, d, J=7.5 Hz), 7.41-7.32 (2H, m), 7.01 (1H, s), 6.92 (1H, d, J=7.5 Hz), 6.81-6.75 (2H, m), 6.54 (1H, s), 6.46 (1H, s), 5.52 (1H, t), 5.33 (2H, s), 3.85 (3H, s), 3.38-3.13 (2H, m); ¹³C-NMR (75 MHz, DMSO-d6) δ (ppm): 197.0, 164.1, 162.7, 157.8, 156.0, 151.0, 149.3, 147.5, 142.0, 133.8, 130.6, 121.4, 120.0, 113.4, 107.2, 102.9, 83.0, 56.3, 43.1; MS (ESI) for (M+H)⁺: 452.1.

Example 5

Preparation of (S,E) 5-hydroxy-2-(3-hydroxy-4-methoxyphenyl)-4-oxochroman-7-yl 3-(5-nitropyridin-2-yl) acrylate acid ester (Compound E)

A mixture of 100 mg (0.16 mmol) hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO₃ was added to adjust the pH of the aqueous solution to about 5. The mixture was then filtered to give an intermediate. The intermediate and 38.8 mg (0.2 mmol) of (E)-3-(5-nitropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 8 hours. The reaction mixture was cooled to room temperature. Water was added to the reaction mixture, and the mixture was then extracted with ethyl acetate. The ethyl acetate layer was concentrated, and purification by flash column chromatograph to give 36.50 mg (yield: 76.4%) desired product with the following structure.

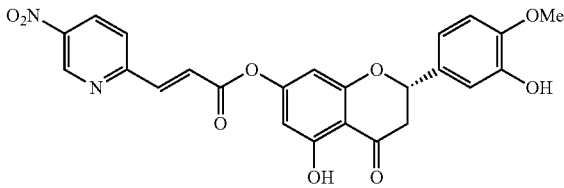 [SMILES: COc1ccc([C@@H]2CC(=O)c3c(O)cc(OC(=O)/C=C/c4ccc([N+](=O)[O-])cn4)cc3O2)cc1O]

¹H-NMR (300 MHz, DMSO-d6) δ (ppm): 9.30 (1H, s), 8.45 (1H, d, J=7.8 Hz), 7.83 (1H, d, J=7.5 Hz), 7.70 (1H, d, J=7.8 Hz), 7.01 (1H, s), 6.92 (1H, d, J=7.5 Hz), 6.81-6.75 (2H, m), 6.54 (1H, s), 6.46 (1H, s), 5.52 (1H, t), 5.33 (2H, s), 3.85 (3H, s), 3.38-3.13 (2H, m); ¹³C-NMR (75 MHz, DMSO-d6) δ (ppm): 197.0, 164.1, 162.7, 160.6, 157.8, 149.3, 147.5, 146.2, 144.2, 142.0, 133.0, 130.6, 121.4, 120.0, 113.4, 107.2, 102.9, 83.0, 56.3, 43.1; MS (ESI) for (M+H)⁺: 479.1.

Example 6

Preparation of (S,E) 5-hydroxy-2-(3-hydroxy-4-methoxyphenyl)-4-oxochroman-7-yl 3-(5-hydroxy-6-methoxypyridin-2-yl) acrylate acid ester (Compound F)

A mixture of 100 mg (0.16 mmol) hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO₃ was added to adjust the pH of the aqueous solution to about 5. The mixture was then filtered to give an intermediate. The intermediate and 39.0 mg (0.2 mmol) of (E)-3-(5-hydroxy-6-methoxypyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 4 hours. The reaction mixture was cooled to room temperature. Water was added to the reaction mixture, and the mixture was then extracted with ethyl acetate. The ethyl acetate layer was concentrated, and purification by flash column chromatograph to give 19.50 mg (yield: 40.7%) desired product with the following structure.

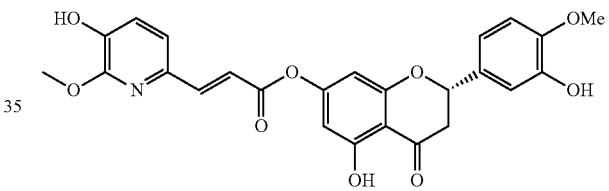

¹H-NMR (300 MHz, DMSO-d6) δ (ppm): 7.83 (1H, d, J=7.5 Hz), 7.17 (1H, d, J=7.8 Hz), 7.01 (1H, s), 6.92 (1H, d, J=7.5 Hz), 6.81-6.75 (2H, m), 6.60 (1H, d, J=7.8 Hz), 6.54 (1H, s), 6.46 (1H, s), 5.52 (1H, t), 5.33 (3H, s), 4.07 (3H, s), 3.85 (3H, s), 3.38-3.13 (2H, m); ¹³C-NMR (75 MHz, DMSO-d6) δ (ppm): 197.0, 164.1, 162.7, 160.0, 157.8, 149.3, 147.5, 146.2, 144.2, 142.0, 130.6, 126.8, 121.4, 120.0, 113.4, 109.3, 107.2, 102.9, 83.0, 56.3, 54.6, 43.1; MS (ESI) for (M+H)⁺: 480.1.

Example 7

Preparation of (S,E) 2-(3,4-dimethoxyphenyl)-5-hydroxy-4-oxochroman-7-yl 3-(pyridin-2-yl) acrylate acid ester (Compound G)

A mixture of 100 mg (0.16 mmol) hesperidin, 0.2 g Na₂CO₃ and 50 mL acetone were added to a reaction flask, and stirred in ice water bath. 1 g methyl iodide was added to the reaction mixture, and the reaction mixture was then stirred at room temperature for 24 hours. 50 mL NaHCO₃ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO₃ was added to adjust the pH of the aqueous solution to about 5. The mixture was then filtered to give an intermediate. The intermediate and 30.0 mg (0.2 mmol) of (E)-3-(pyridin-2-yl) acrylic acid were dissolved in 40 mL DMF. 0.5 g DCC was added as a dehydrating agent. 0.2 g potassium hydroxide was added to the reaction mixture, and reaction mixture was refluxed at 60-100° C. for 5 hours. The reaction mixture was cooled to room temperature. Water was added to the reaction mixture, and the mixture was then extracted with ethyl acetate. The ethyl acetate layer was concentrated, and purification by flash column chromatograph to give 15.50 mg (yield: 33.61%) desired product with the following structure.

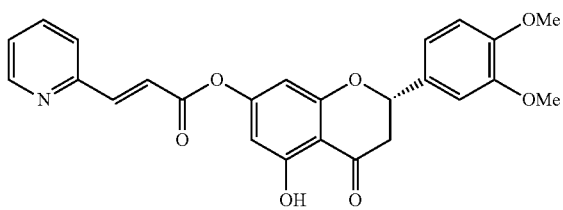 [SMILES: COc1ccc([C@@H]2CC(=O)c3c(O)cc(OC(=O)/C=C/c4ccccn4)cc3O2)cc1OC]

$^1$H-NMR (300 MHz, DMSO-d6) δ (ppm): 8.45 (1H, d), 7.83 (1H, d, J=7.5 Hz), 7.41-7.30 (3H, m), 7.05 (1H, s), 6.92 (1H, d, J=7.5 Hz), 6.81 (2H, d), 6.54 (1H, s), 6.46 (1H, s), 5.52 (1H, t), 5.33 (1H, s), 3.85 (6H, s), 3.38-3.13 (2H, m); $^{13}$C-NMR (75 MHz, DMSO-d6) δ (ppm): 197.0, 164.1, 162.7, 157.8, 154.7, 150.1, 148.8, 142.4, 137.1, 130.6, 124.5, 122.9, 121.4, 120.0, 112.8, 109.3, 107.2, 102.9, 83.0, 56.3, 43.1. MS (ESI) for (M+H)$^+$: 448.1.

Example 8

Preparation of (S,E) 2-(3,4-dimethoxyphenyl)-5-hydroxy-4-oxochroman-7-yl 3-(5-methylpyridin-2-yl) acrylate acid ester (Compound H)

A mixture of 100 mg (0.16 mmol) hesperidin, 0.2 g Na$_2$CO$_3$ and 50 mL acetone were added to a reaction flask, and stirred in ice water bath. 1 g methyl iodide was added to the reaction mixture, and the reaction mixture was then stirred at room temperature for 24 hours. 50 mL NaHCO$_3$ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 32.6 mg (0.2 mmol) of (E)-3-(5-methylpyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 4 hours. The reaction mixture was cooled to room temperature. Water was added to the reaction mixture, and the mixture was then extracted with ethyl acetate. The ethyl acetate layer was concentrated, and purification by flash column chromatograph to give 13.60 mg (yield: 31.19%) desired product with the following structure.

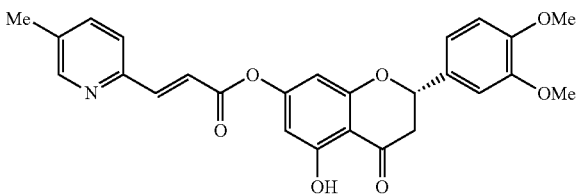 [SMILES: COc1ccc([C@@H]2CC(=O)c3c(O)cc(OC(=O)/C=C/c4ccc(C)cn4)cc3O2)cc1OC]

$^1$H-NMR (300 MHz, DMSO-d6) δ (ppm): 8.40 (1H, s), 7.83 (1H, d, J=7.5 Hz), 7.41 (1H, d, J=7.8 Hz), 7.32 (1H, d, J=7.8 Hz), 7.05 (1H, s), 6.92 (1H, d, J=7.5 Hz), 6.81 (2H, d), 6.54 (1H, s), 6.46 (1H, s), 5.52 (1H, t), 5.33 (1H, s), 3.85 (6H, s), 3.38-3.13 (2H, m), 2.33 (3H, s). $^{13}$C-NMR (75 MHz, DMSO-d6) δ (ppm): 197.0, 164.1, 162.7, 157.8, 152.7, 150.1, 149.7, 148.5, 142.4, 136.3, 132.5, 130.6, 121.4, 120.0, 119.1, 112.8, 109.3, 107.2, 102.9, 83.0, 56.3, 43.1, 18.1. MS (ESI) for (M+H)$^+$: 462.2.

Example 9

Preparation of (S,E) 2-(3,4-dimethoxyphenyl)-5-hydroxy-4-oxochroman-7-yl 3-(5-chloropyridin-2-yl) acrylate acid ester (Compound I)

A mixture of 100 mg (0.16 mmol) hesperidin, 0.2 g Na$_2$CO$_3$ and 50 mL acetone were added to a reaction flask, and stirred in ice water bath. 1 g methyl iodide was added to the reaction mixture, and the reaction mixture was then stirred at room temperature for 24 hours. 50 mL NaHCO$_3$ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 36.7 mg (0.2 mmol) of (E)-3-(5-chloropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 6 hours. The reaction mixture was cooled to room temperature. Water was added to the reaction mixture, and the mixture was then extracted with ethyl acetate. The ethyl acetate layer was concentrated, and purification by flash column chromatograph to give 18.73 mg (yield: 41.36%) desired product with the following structure.

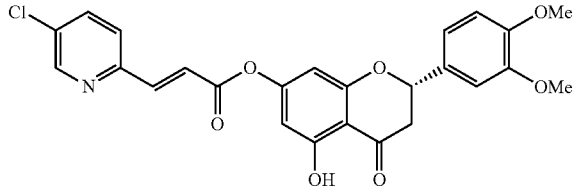 [SMILES: COc1ccc([C@@H]2CC(=O)c3c(O)cc(OC(=O)/C=C/c4ccc(Cl)cn4)cc3O2)cc1OC]

$^1$H-NMR (300 MHz, DMSO-d6) δ (ppm): 8.53 (1H, s), 7.83 (1H, d, J=7.5 Hz), 7.75 (1H, d, J=7.6 Hz), 7.60 (1H, d, J=7.6 Hz), 7.01 (1H, s), 6.92 (1H, d, J=7.5 Hz), 6.81 (2H, d), 6.54 (1H, s), 6.46 (1H, s), 5.52 (1H, t), 5.33 (1H, s), 3.85 (6H, s), 3.38-3.13 (2H, m); $^{13}$C-NMR (75 MHz, DMSO-d6) δ (ppm): 197.0, 164.1, 162.7, 157.8, 153.1, 151.5, 150.1, 148.5, 142.4, 135.8, 132.5, 130.6, 121.4, 119.1, 112.8, 109.3, 107.2, 102.9, 83.0, 56.3, 43.1; MS (ESI) for (M+H)$^+$: 482.1.

Example 10

Preparation of (S,E) 2-(3,4-dimethoxyphenyl)-5-hydroxy-4-oxochroman-7-yl 3-(5-fluoropyridin-2-yl) acrylate acid ester (Compound J)

A mixture of 100 mg (0.16 mmol) hesperidin, 0.2 g Na$_2$CO$_3$ and 50 mL acetone were added to a reaction flask, and stirred in ice water bath. 1 g methyl iodide was added to the reaction mixture, and the reaction mixture was then stirred at room temperature for 24 hours. 50 mL NaHCO$_3$ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 33.3 mg (0.2 mmol) of (E)-3-(5-fluoropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 5 hours. The reaction mixture was cooled to room temperature. Water was added to the reaction mixture, and the mixture was then extracted with ethyl acetate. The ethyl acetate layer was concentrated, and purification by flash column chromatograph to give 11.9 mg (yield: 25.58%) desired product with the following structure.

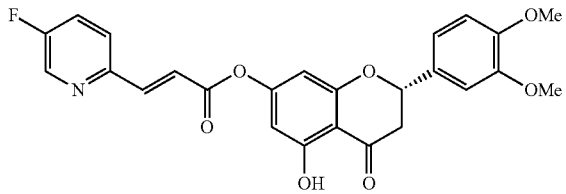 [SMILES: COc1ccc([C@@H]2CC(=O)c3c(O)cc(OC(=O)/C=C/c4ccc(F)cn4)cc3O2)cc1OC]

$^1$H-NMR (300 MHz, DMSO-d6) δ (ppm): 8.36 (1H, d), 7.83 (1H, d, J=7.5 Hz), 7.41-7.32 (2H, m), 7.01 (1H, s), 6.92 (1H, d, J=7.5 Hz), 6.81 (2H, d), 6.54 (1H, s), 6.46 (1H, s), 5.52 (1H, t), 5.33 (1H, s), 3.85 (6H, s), 3.38-3.13 (2H, m); $^{13}$C-NMR (75 MHz, DMSO-d6) δ (ppm): 197.0, 164.1, 162.7, 157.8, 156.0, 150.6, 149.0, 142.0, 133.8, 130.6, 121.4, 119.5, 112.4, 109.6, 107.2, 102.9, 83.0, 56.3, 43.1; MS (ESI) for (M+H)$^+$: 466.1.

Example 11

Preparation of (S,E) 2-(3,4-dimethoxyphenyl)-5-hydroxy-4-oxochroman-7-yl 3-(5-nitropyridin-2-yl) acrylate acid ester (Compound K)

A mixture of 100 mg (0.16 mmol) hesperidin, 0.2 g Na$_2$CO$_3$ and 50 mL acetone were added to a reaction flask, and stirred in ice water bath. 1 g methyl iodide was added to the reaction mixture, and the reaction mixture was then stirred at room temperature for 24 hours. 50 mL NaHCO$_3$ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 38.8 mg (0.2 mmol) of (E)-3-(5-nitropyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 5 hours. The reaction mixture was cooled to room temperature. Water was added to the reaction mixture, and the mixture was then extracted with ethyl acetate. The ethyl acetate layer was concentrated, and purification by flash column chromatograph to give 11.9 mg (yield: 25.58%) desired product with the following structure.

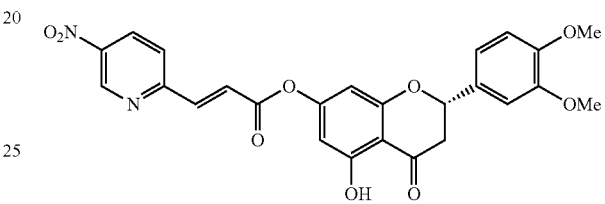

$^1$H-NMR (300 MHz, DMSO-d6) δ (ppm): 9.30 (1H, s), 8.45 (1H, d, J=7.8 Hz), 7.83 (1H, d, J=7.5 Hz), 7.70 (1H, d, J=7.8 Hz), 7.01 (1H, s), 6.92 (1H, d, J=7.5 Hz), 6.81 (2H, d), 6.54 (1H, s), 6.46 (1H, s), 5.52 (1H, t), 5.33 (1H, s), 3.85 (6H, s), 3.38-3.13 (2H, m); $^{13}$C-NMR (75 MHz, DMSO-d6) δ (ppm): 197.0, 164.1, 162.7, 160.6, 157.8, 149.9, 148.5, 146.2, 144.2, 142.0, 133.0, 130.6, 121.4, 119.5, 112.4, 109.2, 107.2, 102.9, 83.0, 56.3, 43.1; MS (ESI) for (M+H)$^+$: 493.1.

Example 12

Preparation of (S,E) 2-(3,4-dimethoxyphenyl)-5-hydroxy-4-oxochroman-7-yl 3-(5-hydroxy-6-methoxypyridin-2-yl) acrylate acid ester (Compound M)

A mixture of 100 mg (0.16 mmol) hesperidin, 0.2 g Na$_2$CO$_3$ and 50 mL acetone were added to a reaction flask, and stirred in ice water bath. 1 g methyl iodide was added to the reaction mixture, and the reaction mixture was then stirred at room temperature for 24 hours. 50 mL NaHCO$_3$ aqueous solution was added to quench the reaction, and the mixture was filtered to give methyl hesperidin. A mixture of methyl hesperidin and 50 mL DMSO were added to a reaction flask. 0.50 mL sulfuric acid was added to mixture, and the mixtured was stirred at 100° C. for 2 hours. 100 mL ice water was added to reaction mixture to quench the reaction, and NaHCO$_3$ was added to adjust the pH of the aqueous solution to about 5. The mixture was then filtered to give an intermediate. The intermediate and 39.0 mg (0.2 mmol) of (E)-3-(5-hydroxy-6-methoxypyridin-2-yl) acrylic acid were dissolved in 40 mL DMF. 0.5 g DCC was added as a dehydrating agent. 0.5 g potassium carbonate was added to the reaction mixture, and reaction mixture was refluxed at 60-100° C. for 6 hours. The reaction mixture was cooled to room temperature. Water was added to the reaction mixture, and the mixture was then extracted with ethyl acetate. The ethyl acetate layer was concentrated, and purification by flash column chromatograph to give 18.9 mg (yield: 38.33%) desired product with the following structure.

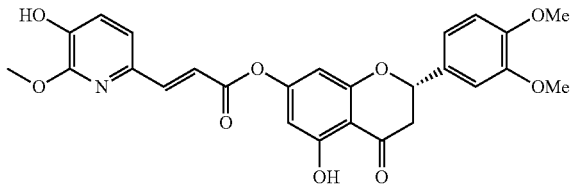 [SMILES: COc1ccc([C@@H]2CC(=O)c3c(O)cc(OC(=O)/C=C/c4ccc(O)c(OC)n4)cc3O2)cc1OC]

$^1$H-NMR (300 MHz, DMSO-d6) δ (ppm): 7.83 (1H, d, J=7.5 Hz), 7.17 (1H, d, J=7.8 Hz), 7.01 (1H, s), 6.92 (1H, d, J=7.5 Hz), 6.81 (2H, d), 6.60 (1H, d, J=7.8 Hz), 6.54 (1H, s), 6.46 (1H, s), 5.52 (1H, t), 5.33 (2H, s), 4.07 (3H, s), 3.85 (6H, s), 3.38-3.13 (2H, m); $^{13}$C-NMR (75 MHz, DMSO-d6) δ (ppm): 197.0, 164.1, 162.7, 159.5, 157.8, 149.5, 148.5, 146.2, 144.0, 142.0, 130.6, 126.8, 121.4, 119.5, 112.4, 109.3, 107.2, 102.9, 83.0, 56.3, 54.6, 43.1; MS (ESI) for $(M+H)^+$: 494.1.

Example 13

The anti-tumor activity test of the compounds of the present invention

The compounds of the present invention were subjected to tumor cell proliferation inhibition test, and the conventional MTT method was used as the test method.

Cell lines selected are nonismall cell lung cancer cells (A549), human hepatocellular carcinoma cells (SMMC-7721), human glioma cells (U251), human gastric adenocarcinoma cells (SGC-7901), and human breast cancer cells (MCF-7). The culture medium was DMEM+15% NBS+ double antibody.

Preparation of the sample solutions: compounds were dissolved in DMSO (Merck), and PBS (−) was add to 100 μL of the solution or homogeneous suspension. The solution or suspension was diluted with DMSO and PBS(−) to final concentrations of 0.1, 1, 10, 20, 40, 60, 80, 100 μmol/L.

Anti-tumor agent cytarabine (Ara-C) was used as control and was prepared in the same way as the compounds.

Cell culture: adherent growth Tumor cells were cultured in 1640 medium containing 10% inactivated neonatal bovine serum and penicillin, streptomycin (1 million U/L), placed in carbon dioxide incubator at 37° C., 5% $CO_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μL of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Differen Tumor Cells $IC_{50}$ (unit: μmol/L)

| Compounds | $IC_{50}$ (μmol/L) | | | | |
| --- | --- | --- | --- | --- | --- |
| | A549 | SMMC-7721 | U251 | SGC-7901 | MCF-7 |
| A | 35.10 ± 0.47 | 46.75 ± 1.56 | >100 | 89.88 ± 1.02 | 43.13 ± 1.31 |
| B | >100 | 67.12 ± 1.74 | 46.00 ± 0.21 | >100 | >100 |
| C | 5.54 ± 0.39 | 86.87 ± 2.28 | 11.72 ± 0.45 | 18.42 ± 1.71 | 22.68 ± 0.32 |
| D | 7.28 ± 0.13 | 12.83 ± 1.37 | 57.13 ± 0.47 | 67.13 ± 0.28 | 23.71 ± 1.50 |
| E | >100 | >100 | >100 | >100 | >100 |
| F | >100 | 23.71 ± 1.50 | >100 | >100 | 92.12 ± 2.73 |
| G | 69.13 ± 0.36 | >100 | 28.47 ± 0.45 | >100 | >100 |
| H | >100 | 47.88 ± 0.4 | >100 | 63.87 ± 2.28 | >100 |
| I | >100 | 63.87 ± 2.28 | 63.87 ± 2.28 | 16.13 ± 0.47 | >100 |
| J | 46.26 ± 0.47 | 84.31 ± 0.47 | 25.13 ± 0.47 | >100 | 16.13 ± 0.47 |
| K | >100 | >100 | >100 | >100 | >100 |
| M | >100 | 33.27 ± 2.08 | >100 | 63.87 ± 0.4 | 18.62 ± 1.01 |
| Ara-C | >100 | 18.29 ± 0.64 | 19.17 ± 0.39 | 67.62 ± 3.73 | 76.87 ± 1.78 |

The results show that the compounds of the present invention exhibit inhibitory effect on the cells. Compounds A, B, C, D, F, G, H, I, J, M have equal or better activities than Ara-C in some cell lines tested. In summary, these compounds can be used in cancer research and to treat various cancers.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A hesperetin aza-cinnamic acid derivative having the following formula (I):

(I)
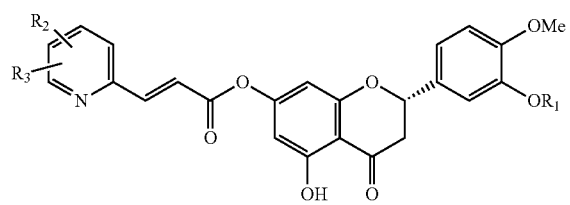

wherein $R_1$ is H or alkyl, and $R_2$ and $R_2$ are independently H, alkyl, hydroxy, halogen, nitro, or alkoxy.

2. The hesperetin aza-cinnamic acid derivative of claim 1, wherein the hesperetin aza-cinnamic acid derivative has the following formula (II):

(II)
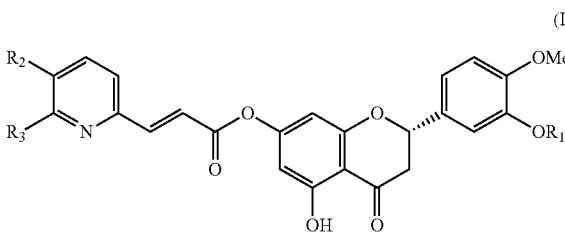

wherein $R_1$ is H or alkyl, $R_2$ is H, alkyl, hydroxy, halogen, nitro, or alkoxy, and $R_3$ is H or alkoxy.

3. The hesperetin aza-cinnamic acid derivative of claim 2, wherein the hesperetin aza-cinnamic acid derivative is selected from the group consisting of A
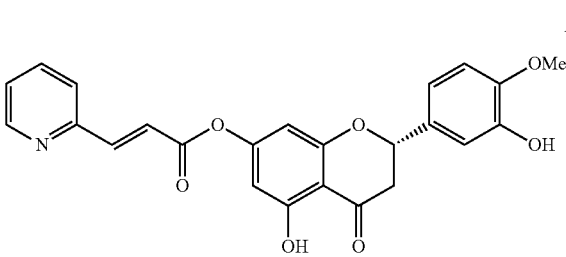

B
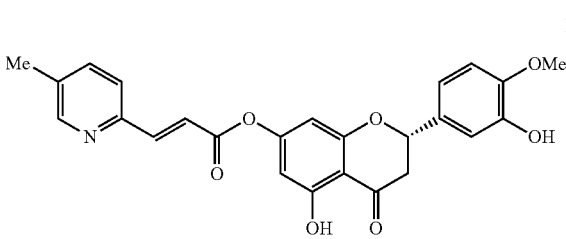

C
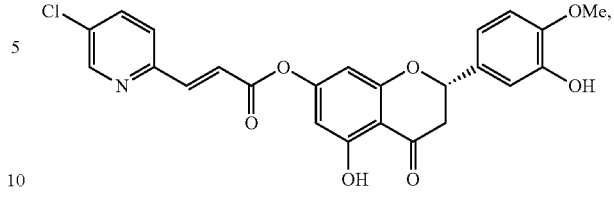

D
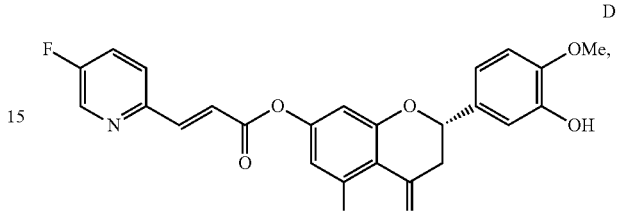

E
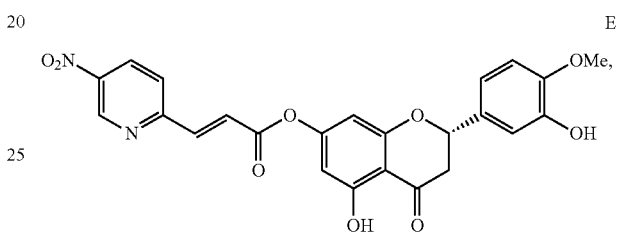

F
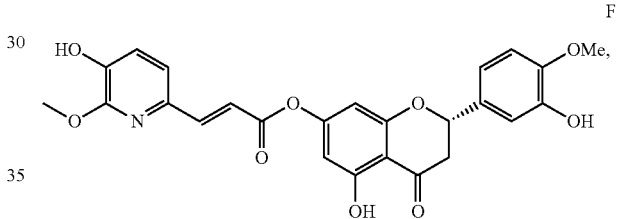

G
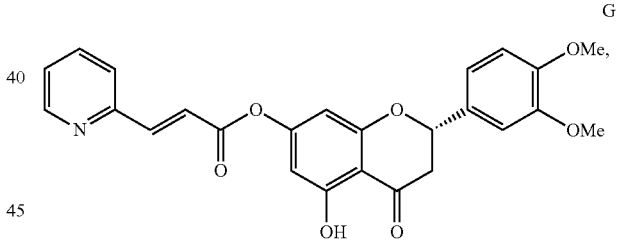

H
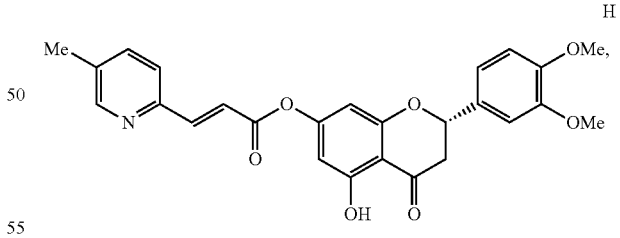

I
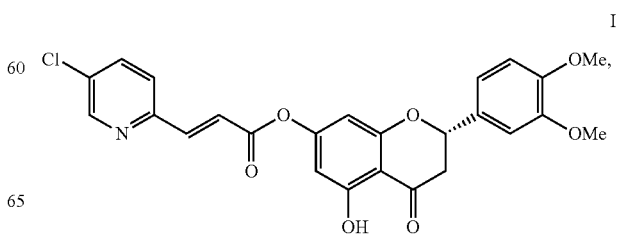

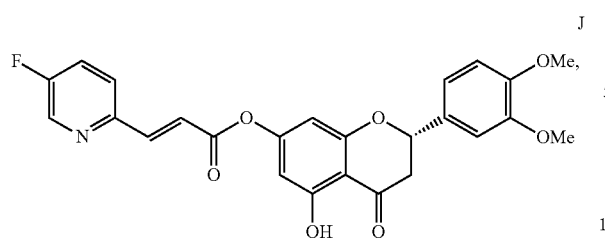

J

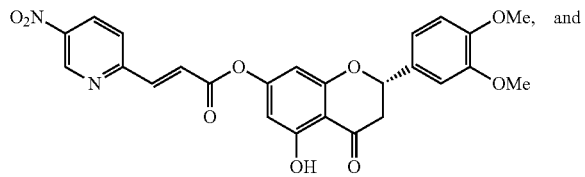

K

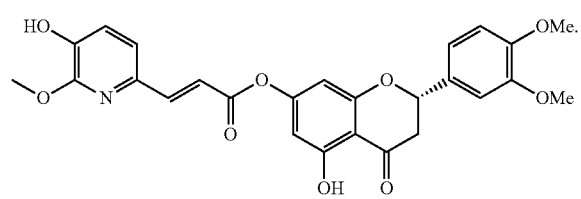

M

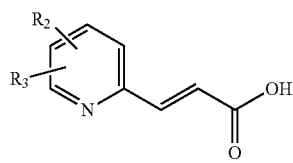

(V)

to obtain a hesperetin aza-cinnamic acid derivative of formula (I):

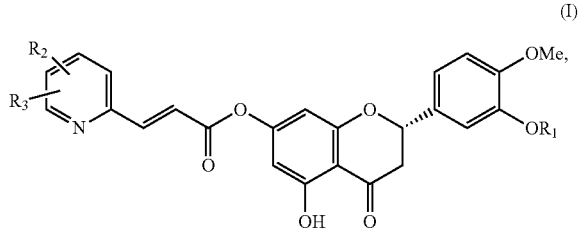

(I)

wherein $R_1$ is H or alkyl, and $R_2$ and $R_3$ are independently H, alkyl, hydroxy, halogen, nitro, or alkoxy.

5. The method of claim 4, wherein in step (1), after the reaction of the compound of formula (III) with the acid is complete, the compound of formula (IV) is precipitated at a pH value of 5.

6. The method of claim 4, wherein in step (1), the acid is hydrochloric acid or sulfuric acid.

7. The method of claim 4, wherein in step (1), the reaction of the compound of formula (III) with the acid is conducted in an organic solvent selected from the group consisting of DMSO, acetonitrile, THF, DMF, and acetone.

8. The method of claim 4, wherein in step (1), the reaction of the compound of formula (III) with the acid is conducted at 90-110° C.

9. The method of claim 4, wherein in step (2), the reaction of the compound of formula (IV) with the compound of formula (V) is conducted in the presence of a base and DCC.

10. The method of claim 9, wherein in step (2), the base is sodium carbonate.

11. The method of claim 4, wherein in step (2), the reaction of the compound of formula (IV) with the compound of formula (V) is conducted in an organic solvent selected from the group consisting of DMSO, acetonitrile, THF, DMF, and acetone.

12. The method of claim 4, wherein in step (2), a molar ratio of the compound of formula (IV) and the compound of formula (V) is 1:1 to 1:1.5.

13. The method of claim 12, wherein in step (2), the molar ratio of the compound of formula (IV) and the compound of formula (V) is 1:2.

14. The method of claim 12, wherein in step (2), the reaction of the compound of formula (IV) with the compound of formula (V) is conducted at 60-100° C.

15. A method of using the hesperetin aza-cinnamic acid derivative of claim 1 in antitumor drug research, development, and application.

16. A method of using the hesperetin aza-cinnamic acid derivative of claim 1 in treating human Lung cancer, liver cancer, glioma, gastric adenocarcinoma or breast cancer.

4. A method of preparing hesperetin aza-cinnamic acid derivatives with antitumor activities comprising the following steps:

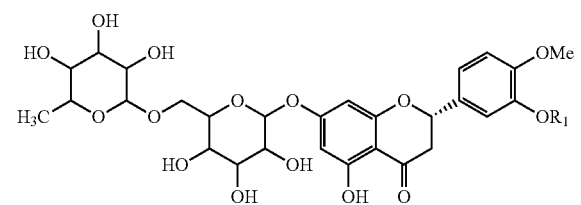

(1) reacting a compound of formula (III):
(III) with an acid to obtain a compound of formula (IV):

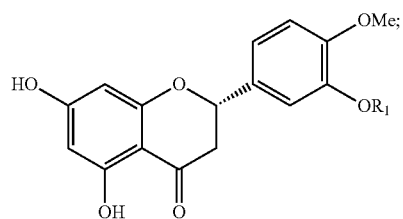

(IV)

and
(2) reacting the compound of formula (IV) with a compound of formula (V):

* * * * *